(12) United States Patent
Ash

(10) Patent No.: US 8,409,864 B2
(45) Date of Patent: Apr. 2, 2013

(54) AMMONIA SENSOR AND SYSTEM FOR USE

(75) Inventor: Stephen R. Ash, Lafayette, IN (US)

(73) Assignee: Renal Solutions, Inc., Warrendale, PA (US)

( * ) Notice: Subject to any disclaimer, the term of this patent is extended or adjusted under 35 U.S.C. 154(b) by 1728 days.

(21) Appl. No.: 11/443,709

(22) Filed: May 31, 2006

(65) Prior Publication Data

US 2007/0161113 A1    Jul. 12, 2007

Related U.S. Application Data

(60) Provisional application No. 60/756,783, filed on Jan. 6, 2006.

(51) Int. Cl.
| G01N 33/00 | (2006.01) |
| G01N 21/00 | (2006.01) |
| G01N 21/77 | (2006.01) |
| G01N 1/22 | (2006.01) |

(52) U.S. Cl. ........ 436/113; 436/106; 436/164; 436/165; 436/166; 436/167; 422/82.05; 422/83; 422/84; 422/85; 422/86; 422/87; 422/88; 604/4.01; 604/504; 600/364; 600/365

(58) Field of Classification Search .................. None
See application file for complete search history.

(56) References Cited

U.S. PATENT DOCUMENTS

| 3,011,874 | A | 12/1961 | Deutsch |
| 3,427,225 | A | 2/1969 | Harvill et al. |
| 3,528,780 | A | 9/1970 | Radawski |
| 3,531,254 | A | 9/1970 | Okuda |
| 3,853,477 | A | * | 12/1974 | Block et al. .................. 422/85 |
| 3,873,269 | A | 3/1975 | Kraffczyk et al. |
| 3,923,757 | A | 12/1975 | Salyer et al. |
| RE30,267 | E | 5/1980 | Bruschi |
| 4,223,089 | A | 9/1980 | Rothe et al. |
| 4,244,787 | A | 1/1981 | Klein et al. |
| 4,548,906 | A | 10/1985 | Sekikawa et al. |
| 4,632,435 | A | 12/1986 | Polyak |
| 4,640,820 | A | 2/1987 | Cooper |
| 4,661,246 | A | 4/1987 | Ash et al. |
| 4,859,378 | A | 8/1989 | Wolcott |
| 5,008,078 | A | 4/1991 | Yaginuma et al. |
| 5,258,314 | A | * | 11/1993 | Skerratt .................. 436/165 |
| 5,286,624 | A | 2/1994 | Terashima et al. |
| 5,308,315 | A | 5/1994 | Khuri et al. |
| 5,401,238 | A | 3/1995 | Pirazzoli |
| 5,405,315 | A | 4/1995 | Khuri et al. |
| 5,507,723 | A | 4/1996 | Keshaviah |
| 5,518,623 | A | 5/1996 | Keshaviah et al. |
| 5,662,806 | A | 9/1997 | Keshaviah et al. |
| 5,698,083 | A | 12/1997 | Glass |
| 5,788,846 | A | 8/1998 | Sternby |
| 5,858,186 | A | 1/1999 | Glass |
| 5,945,343 | A | 8/1999 | Munkholm |

(Continued)

*Primary Examiner* — Neil N Turk
(74) *Attorney, Agent, or Firm* — Fish & Richardson P.C.

(57) ABSTRACT

An ammonia gas sensing device includes a housing defining a fluid flow path. The fluid flow path includes a fluid inlet, a fluid outlet, and an access port. A gas permeable/liquid impermeable membrane is mounted on and sealed against the housing at the access port such that the membrane is exposed to the fluid flow path but fluid is blocked from flowing outward of the access port around rather than through the membrane. An ammonia sensor is mounted on the housing at the access port in a position outward of the membrane. A system for using the ammonia sensing device includes the ammonia gas sensing device, a light source directed at the ammonia sensor, a photo detector to measure the light reflected off the ammonia sensor from the light source, and a controller for controlling the light source and optical sensor.

50 Claims, 5 Drawing Sheets

U.S. PATENT DOCUMENTS

| | | |
|---|---|---|
| 6,013,529 A | 1/2000 | Munkholm |
| 6,107,099 A | 8/2000 | Munkholm |
| 6,219,567 B1 | 4/2001 | Eggers et al. |
| 6,479,019 B1 | 11/2002 | Goldstein et al. |
| 6,666,840 B1 | 12/2003 | Falkvall et al. |
| 2003/0113931 A1 | 6/2003 | Pan et al. |
| 2003/0113932 A1 | 6/2003 | Sternberg et al. |
| 2003/0216677 A1 | 11/2003 | Pan et al. |
| 2004/0019312 A1 | 1/2004 | Childers et al. |
| 2004/0100376 A1 | 5/2004 | Lye et al. |
| 2004/0176672 A1 | 9/2004 | Silver et al. |

\* cited by examiner

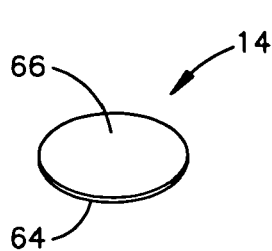 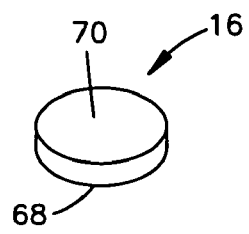 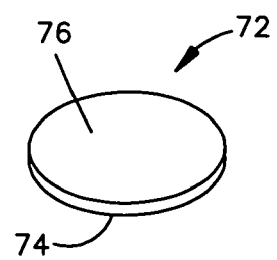
Fig.4　　　　Fig.5　　　　Fig.6
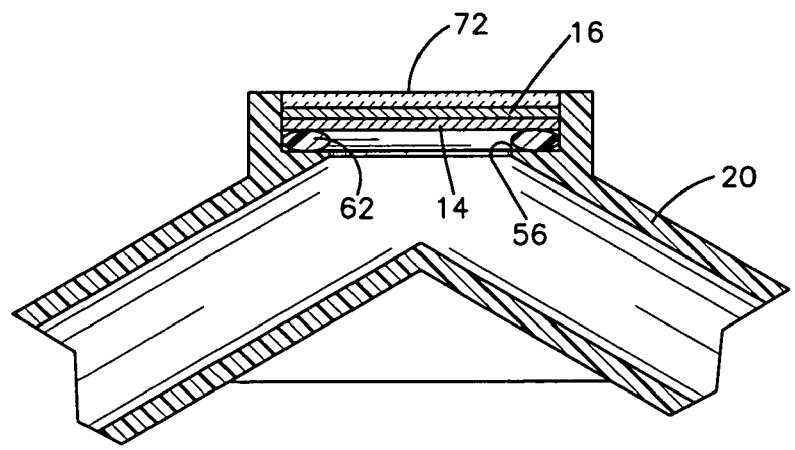
Fig.7
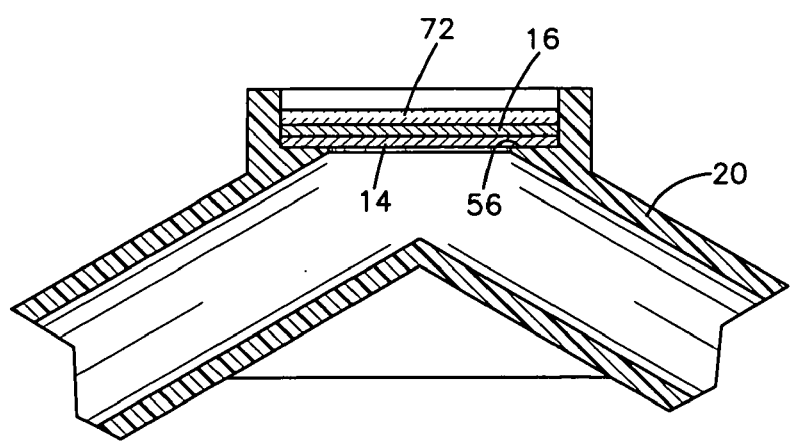
Fig.8

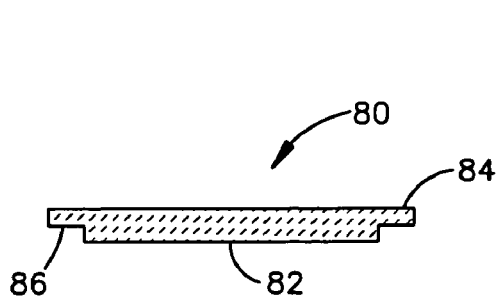
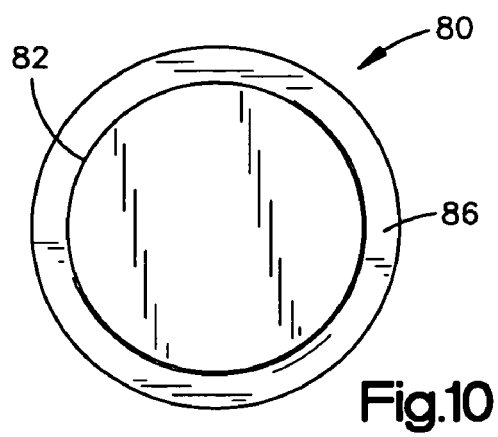
Fig.9
Fig.10
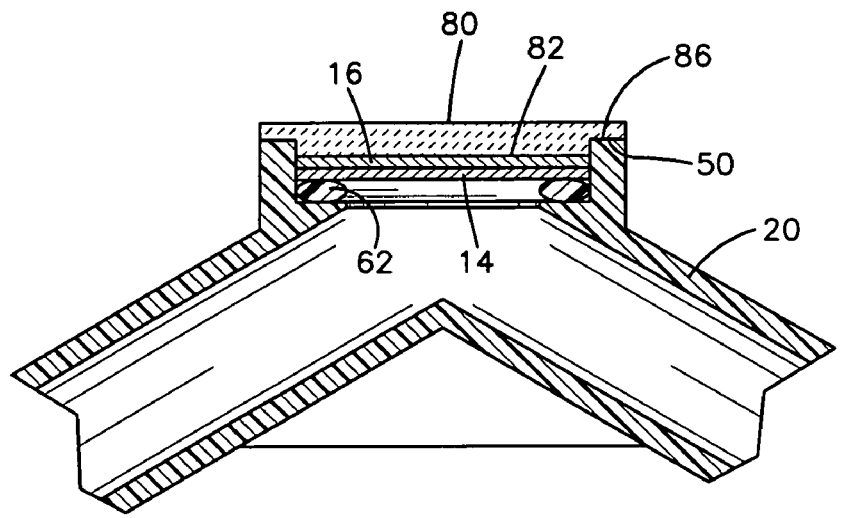
Fig.11
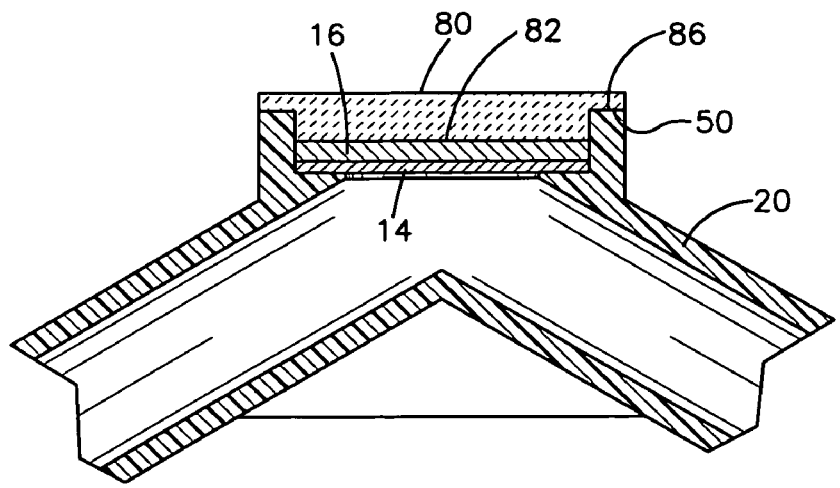
Fig.12

AMMONIA SENSOR AND SYSTEM FOR USE

RELATED APPLICATIONS

This application claims priority to U.S. Provisional Application Ser. No. 60/756,783, filed Jan. 6, 2006, which is hereby incorporated by reference.

TECHNICAL FIELD

This technology relates to the use of chemical based sensors to detect ammonia gas in fluids.

BACKGROUND

Sorbent based blood dialysis systems operate by circulating blood and dialysate fluid through a dialyzer on opposite sides of a membrane within the dialyzer. Blood waste compounds can move across the membrane from the blood side to the dialysate side. The dialysate fluid containing blood waste compounds can then be recycled by removing or breaking down the blood waste compounds. The process for removing urea, for example, can involve exposing the dialysate fluid to a material that breaks down urea into ammonium ions and carbonate. The byproduct ammonium ions are then removed by binding to an ion exchange material such as zirconium phosphate. Even though the ammonium ions are safely and easily removed by this process, it is sometimes desirable to monitor the presence of ammonium ions in dialysate fluid.

SUMMARY

The claimed invention provides an ammonia gas detecting device for monitoring the gaseous ammonia in a fluid. The detecting device includes a housing defining a fluid flow path. The fluid flow path includes a fluid inlet, a fluid outlet, and an access port located between the fluid inlet and fluid outlet. A gas permeable/liquid impermeable membrane is mounted on the housing at the access port. The membrane is exposed to the fluid flow path, but fluid is blocked from flowing outward of the access port around rather than through the membrane. An ammonia sensor is mounted on the housing at the access port in a position outward of the membrane.

The claimed invention further provides a system for using the ammonia gas detecting device to monitor the gaseous ammonia in a fluid. The system includes a light source directed at the ammonia sensor, a photo detector to measure the light reflected off the ammonia sensor from the light source, and a controller for controlling the light source and optical sensor.

BRIEF DESCRIPTION OF THE DRAWINGS

FIG. 4 is a perspective view of a membrane in the device of FIG. 1.

FIG. 5 is a perspective view of an ammonia sensor in the device of FIG. 1.

FIG. 6 is a perspective view of a lens in the device of FIG. 1.

FIGS. 7 and 8 are enlarged partial views of alternative configurations for the device shown in FIG. 1.

FIG. 9 is a sectional view of an alternative lens.

FIG. 10 is a perspective view of the lens shown in FIG. 9.

FIGS. 11 and 12 also are enlarged partial views of alternative configurations for the device shown in FIG. 1.

DETAILED DESCRIPTION

Figure 1:
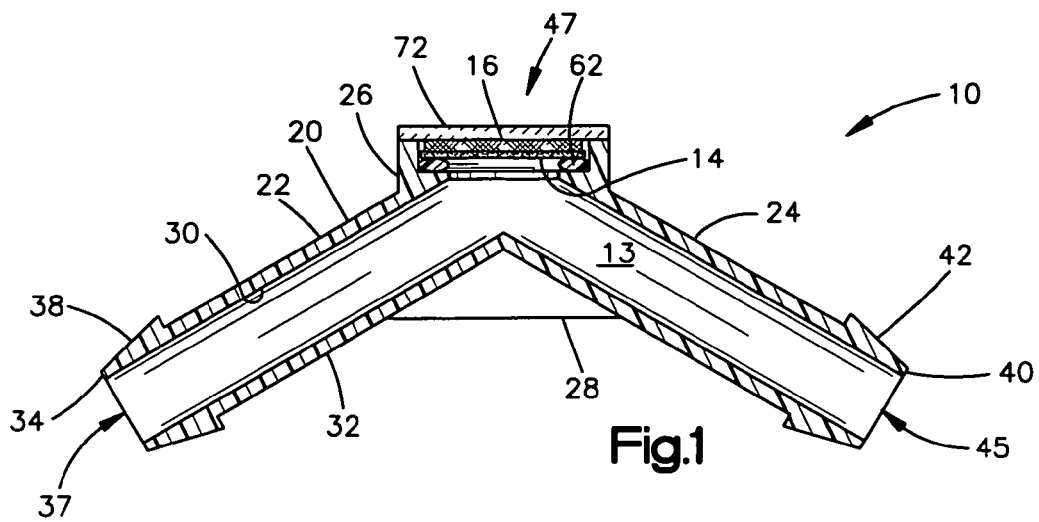
FIG. 1 is a sectional view of an example of an ammonia gas detecting device.

The devices shown in the drawings have parts that are examples of the elements recited in the claims. The following description thus includes examples of how a person of ordinary skill in the art can make and use the claimed invention. This description is provided to meet the requirements of written description, enablement, and best mode without imposing limitations that are not recited in the claims.

In the example shown in FIG. 1, an ammonia gas detecting device 10 includes a fluid flow path 13 through which a fluid, such as blood or dialysate fluid, can flow past a liquid impermeable/gas permeable membrane 14. Located outside the membrane 14 is a chemical based ammonia sensor 16 that can react with gaseous ammonia that passes through the membrane 14. The ammonia sensor 16 will provide a detectable change when exposed to gaseous ammonia, thereby indicating the presence of ammonia in the fluid flowing past the membrane 14.

Figure 2:
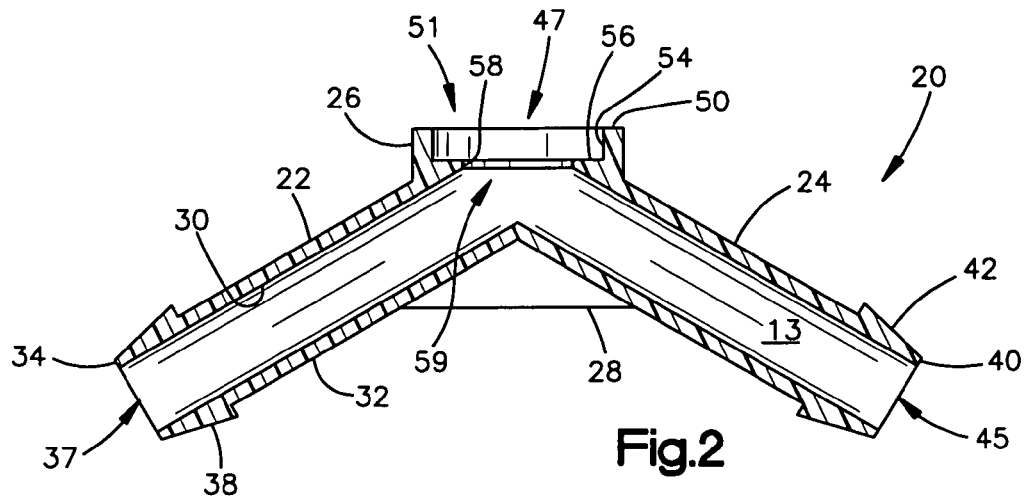
FIG. 2 is a sectional view of a housing that is part of the device of FIG. 1.
Figure 3:
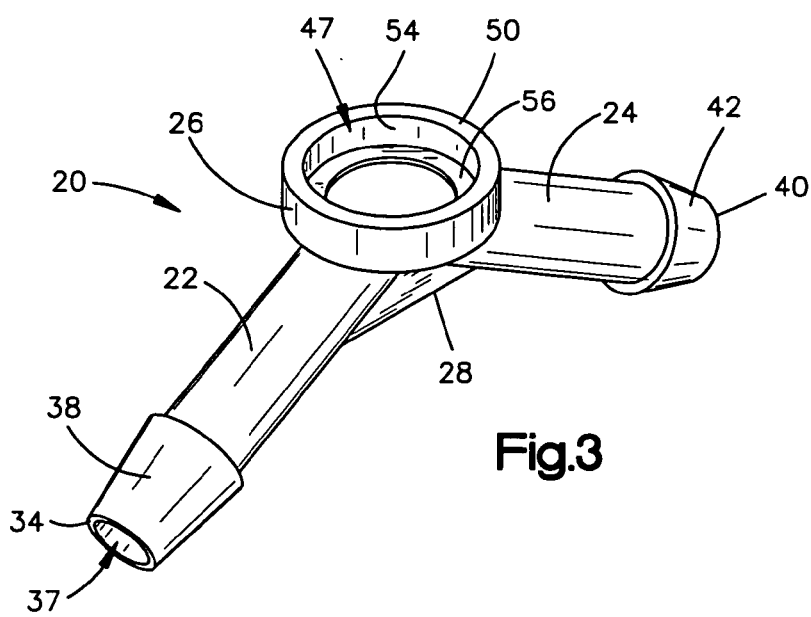
FIG. 3 is a perspective view of the housing shown in FIG. 2.

As shown in FIG. 1, the device 10 has a housing 20 defining the fluid flow path 13. The housing 20 in this particular example is a one-piece unitary structure made of plastic. As shown separately in FIGS. 2 and 3, the housing 20 has first and second sections 22 and 24 respectively defining first and second sections of the fluid flow path 13. The housing 20 further has a corner portion 26 at which the first and second sections 22 and 24 intersect at an angle. A stiffening web 28 extends between the two sections 22 and 24.

The first section 22 of the housing 20 has cylindrical inner and outer surfaces 30 and 32 providing it with a straight tubular configuration along its entire length. An annular end surface 34 of the first section 22 defines a circular inlet 37 to the fluid flow path 13. The end surface 34 is part of a flared end portion 38 of the first section 22 that is configured for connection to a flexible hydraulic line or hose.

The second section 24 of the housing 20 is configured in the mirror image of the first section 22, and thus has a straight tubular configuration along its entire length. The annular end surface 40 on the hose-connecting portion 42 of the second section 24 defines an outlet 45 from the fluid flow path 13.

The corner portion 26 of the housing defines an access port 47. An annular outer end surface 50 of the corner portion 26 defines the open outer end 51 of the access port 47. A cylindrical inner surface 54 extends axially inward from the outer end surface 50, and an annular shoulder surface 56 extends radially inward from the cylindrical surface 54. An edge 58 of the shoulder surface 56 defines the open inner end 59 of the access port 47. This example of an access port 47 is thus configured as a counterbore.

As shown in FIG. 1, an O-ring seal 62 is mounted on the housing 20 on the shoulder surface 56 in the access port 47. The membrane 14 is mounted on the housing 20 in a position outward of the O-ring seal 62 toward the open outer end 51 of the access port 47. Accordingly, the O-ring seal 62 is located between shoulder surface 56 and the membrane 14. As shown in FIG. 4, the membrane 14 is disc shaped with an inner surface 64 and an outer surface 66. The membrane 14 is gas permeable and liquid impermeable, and includes many fine passages extending through from the inner surface 64 to the outer surface 66. These passages are large enough for ammonia gas to pass through, but are small enough to block liquid from passing through. An example of such a gas permeable and liquid impermeable membrane is GoreTex®. Referring again to FIG. 1, the seals formed by and between the O-ring seal 62, the shoulder surface 56, and the membrane 14 prevent fluid from flowing outward from the access port 47 around rather than through the membrane 14.

The ammonia sensor 16 is mounted on the housing 20 at the access port 47 in a position outward of the membrane 14. As shown in FIG. 5, the ammonia sensor 16 is disc shaped with an inner surface 68 and an outer surface 70. The ammonia sensor 16 includes a chemical indicator substance that will undergo a detectable change, such as a visual color change, when the ammonia sensor 16 is exposed to gaseous ammonia. An example of a suitable chemical indicator substance is a mixture of bromocresol green and malonic acid. The bromocresol green/malonic acid chemical indicator substance changes color from yellow to blue upon exposure to gaseous ammonia. The chemical indicator substance can be supported by a suitable substrate such as cellulose paper. An example of a suitable paper substrate is Whatman® Grade 1 filter paper. Thus, an example of an ammonia sensor 16 is Whatman® Grade 1 filter paper treated with about 1 μL of a malonic acid (about 8 mM)/bromocresol green sodium salt (about 0.83 mM) solution in ethanol.

Referring again to FIG. 1, a lens 72 is mounted on the housing 20 at the annular outer end surface 50 of the access port 47. As shown in FIG. 6, the lens 72 is disc shaped with an inner surface 74 and an outer surface 76. The lens can be an optically clear polymer such as polycarbonate. The lens 72, ammonia sensor 16, membrane 14, and O-ring seal 62 are secured to the housing with an optically transparent adhesive such as Loctite® FLASHCURE™ 4307. The adhesive bonds are omitted from the drawing for clarity of illustration.

The lens 72 could be configured to be mounted on the housing 20 within the access port 47 as shown in FIG. 7. In this configuration, the diameter of the lens 72 is large enough that the outer edge of the lens 72 extends over the shoulder surface 56 around its entire periphery. The O-ring 62 and other components function as described above.

An alternative ammonia sensor configuration can also be utilized when the lens 72 is configured to be mounted on the housing 20 within the access port 47 as shown in FIG. 7. This ammonia sensor configuration is shown in FIG. 8. A seal is formed by securing the lens 72 to the housing 20 such that a compressive force is exerted by and between the outer edge of the lens 72 and the shoulder surface 56. The compressive force exerted by the lens 72 also compresses the outer edge of the membrane 14, which overlaps the shoulder surface 56, tightly against the shoulder surface 56 to form a compressive seal between the membrane 14 and the shoulder surface 56. The compressive seal between the membrane 14 and the shoulder surface 56 blocks fluid from flowing outward of the access port 47 around rather than through the membrane 14. The lens 72 can be secured to the housing 20, for example, with an adhesive or by ultrasonic staking.

FIGS. 9 and 10 show an alternative configuration of a lens 80. As shown in FIGS. 9 and 10, this lens 80 has a cylindrical inner portion 82 and a ring-shaped outer rim portion 84. The inner portion 82 is axially thicker than the outer rim potion 84 forming a shelf surface 86.

As shown in FIG. 11, the alternative lens 80 is sized relative to the housing 20 so that when mounted on the housing 20 at the access port 47, the shelf surface 86 of the lens 80 overlaps the outer end surface 50 of the access port 47 around its entire periphery and the annular inner portion 82 of lens 80 extends down within the access port 47. Further, the diameter of the annular inner portion 82 of the lens 80 is large enough that the outer edge of the annular inner portion 82 overlaps the shoulder surface 56 around its entire periphery. In the example shown in FIG. 11, the O-ring 62 and other components function as described above. The lens 80 is secured to the housing 20 at the shelf surface 86 of the lens 80 and the outer end surface 50 of the access port 47. Specifically, the lens 80 is ultrasonically staked to the housing 20 at the periphery of the shelf surface 86. Alternatively, the lens 80 could be secured by an adhesive.

An additional ammonia sensor configuration can be utilized when the annular inner portion 82 of lens 80 is configured to extend down within the access port 47 and the diameter of the annular inner portion 82 is large enough that the outer edge of the annular inner portion 82 overlaps the shoulder surface 56 around its entire periphery as shown in FIG. 11. This ammonia sensor configuration is shown in FIG. 12. A seal is formed by securing the lens 80 to the housing such that a compressive force is exerted between the outer edge of the annular inner portion 82 of the lens 80 and the shoulder surface 56. The compressive force exerted by the lens 80 is transferred through the ammonia sensor 16 from the lens 80 to the membrane 14 and compresses the outer edge of the membrane 14 against the shoulder surface 56. The compressive seal between the membrane 14 and the shoulder surface 56 blocks fluid from flowing outward of the access port 47 around rather than through the membrane 14. In this configuration the thicknesses of the membrane 14, the ammonia sensor 16, and the lens 80 are chosen so that a compressive force sufficient to form a seal between the membrane 14 and the shoulder surface 56 is created before the cylindrical outer rim portion 84 of the lens 80 comes into contact the outer end surface 50 of the access port. The lens 80 can be secured to the housing 20, for example, with an adhesive or by ultrasonic staking.

Figure 13:
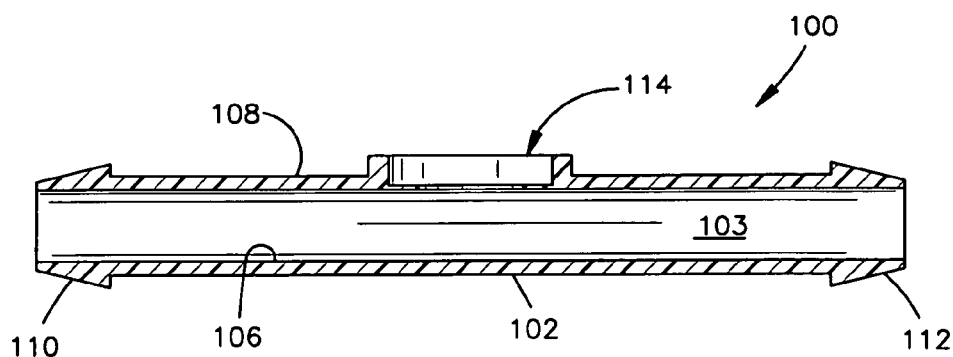
FIGS. 13 and 14 are sectional views of alternative housings for ammonia gas detecting devices.
Figure 14:
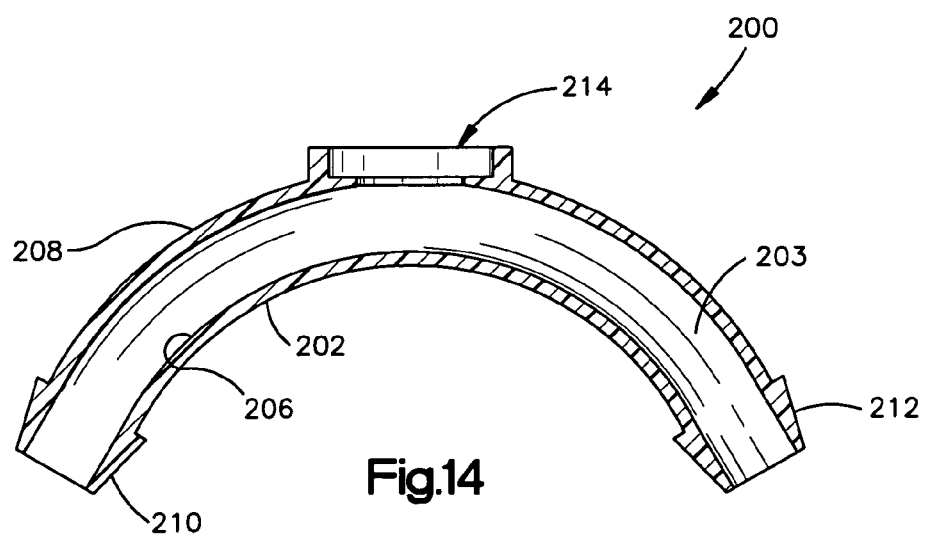

FIGS. 13 and 14 show alternative examples of housings for ammonia detecting devices. The housing 100 shown in FIG. 13 has a tubular portion 102 defining a fluid flow path 103. The tubular portion 102 of the housing 100 has cylindrical inner and outer surfaces 106 and 108 providing it with a straight tubular configuration along its entire length. The end portions 110 and 112 of the tubular portion are configured for connection to flexible hydraulic lines or hoses as described above for the housing 20 shown in FIGS. 2 and 3. The housing 100 has an access port 114 with the same features as the access port 47 described above.

The housing 200 shown in FIG. 14 has a tubular portion 202 defining a curved fluid flow path 203. The tubular portion 202 of housing 200 is curved with cylindrical inner and outer surfaces 206 and 208 providing a curved tubular configuration along its entire length. The end portions 210 and 212 of the tubular portion 202 are configured for connection to flexible hydraulic lines or hoses as described above. The housing 200 has an access port 214 with the same features as the access port 47 described above.

Figure 15:
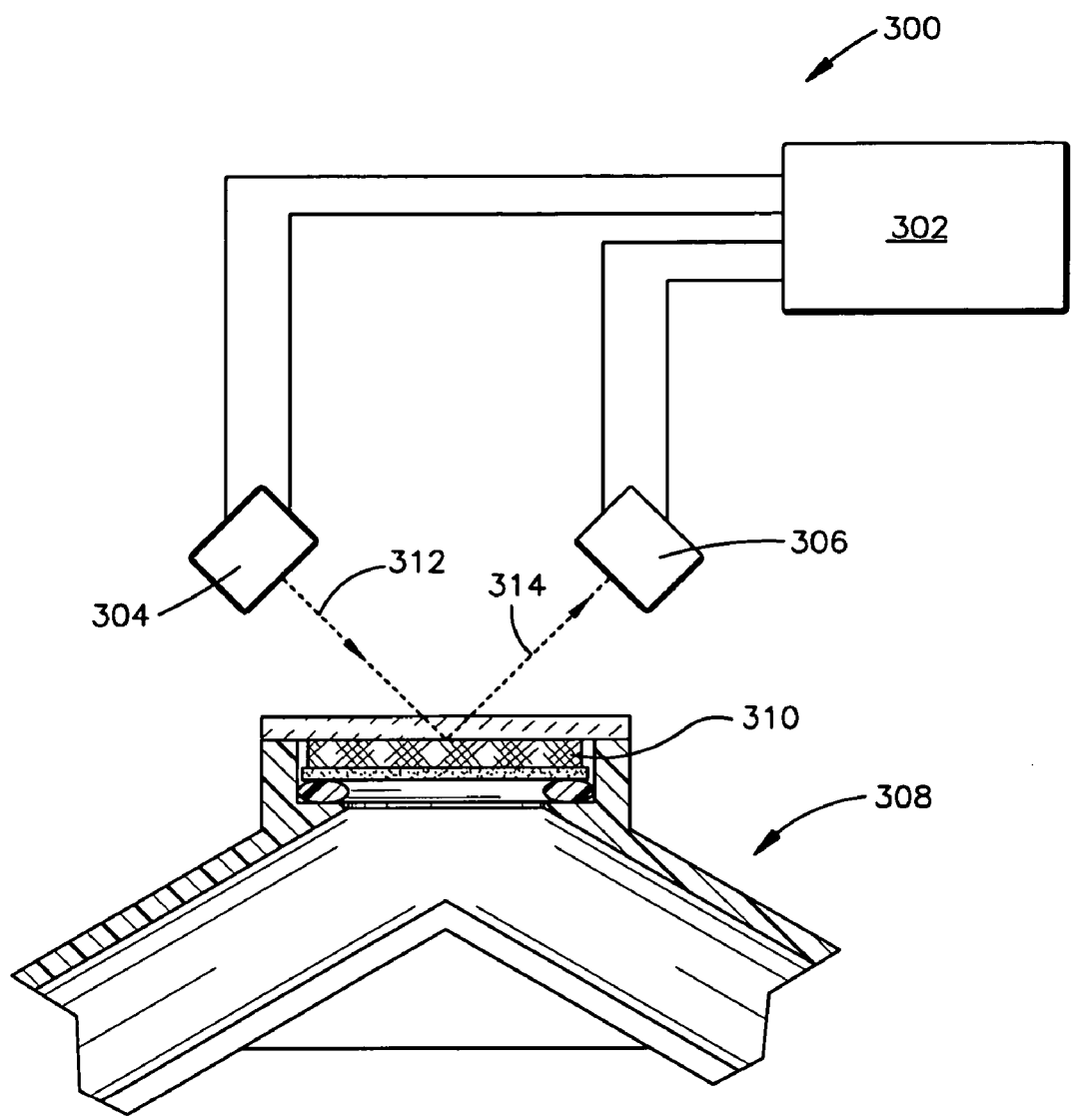
FIG. 15 is a schematic view of a system for monitoring the ammonia gas level in a fluid.

The ammonia gas detecting devices described above can be used in a system for monitoring the ammonia gas level in a fluid. As shown in FIG. 15, an ammonia gas detecting system 300 includes a controller 302, a light source 304, a photo detector 306, and an ammonia gas detecting device 308 that includes an ammonia sensor 310. The ammonia gas detecting device 308 shown for example in FIG. 15 is the same as the device 20 described above with reference to FIG. 1.

As shown in FIG. 15, the controller 302 is operatively interconnected with the light source 304 and photo detector 306. The controller 302 has hardware and/or software configured for operation of those components 304 and 306, and may comprise any suitable programmable logic controller or other control device, or combination of control devices, that is programmed or otherwise configured to perform as recited in the claims. The light source 304 is an LED and the photo detector 306 can be a phototransistor or a light sensitive diode.

In the operation of the system 300 shown in FIG. 15, light from the light source 304, as controlled by the controller 302, is directed to impinge upon the ammonia sensor 310, as indicated by line 312. Light reflected off the ammonia sensor 310 impinges upon the photo detector 306, as indicated by line 314. The intensity of the light impinging on the photo detector 306 can change with changes in the color of the ammonia sensor 310. For example, if the ammonia sensor 310 changes from yellow to blue upon exposure to ammonia gas and the light source 304 is a yellow LED, the intensity of the light reflected off the ammonia sensor 310 will decrease as the color of the ammonia sensor 310 changes from yellow to blue.

The rate at which a detectable change occurs in the ammonia sensor is dependent upon both the sensitivity of the chemical indicator substance and the amount of gaseous ammonia to which the ammonia sensor is exposed. As an example, a useful ammonia sensor will be sensitive enough to detect low levels of gaseous ammonia, but the detectable change, e.g., a transition between colors, will occur gradually in a quantitative-type relationship with the amount of gaseous ammonia detected. When the ammonia sensor changes in a quantitative-type relationship with the level of exposure to gaseous ammonia, the detectable change provides a means for quantifying the amount of gaseous ammonia to which the ammonia sensor has been exposed. Specifically, the ratio of $NH_4^+$ to $NH_3$ in blood at pH 7.3 is approximately 1000 to 1. Thus, when the amount of gaseous ammonia molecules in a fluid, such as blood at a known pH, is known, the amount of ammonium ions in the fluid can be estimated based on a relationship such as that in blood. Another indicator that could be used is a rapid increase in ammonia level over a set period of time.

If, for example, the photo detector 306 is a phototransistor, the decrease in reflected light will result in a decrease in voltage output from the phototransistor. In this example, the controller 302, which is monitoring the phototransistor, will register the decrease. Depending upon any changes in the voltage output, the controller 302 will provide an appropriate indication to the system in which the ammonia gas detecting system is operating and the system can then act accordingly. If the controller 302 also controls the larger system, it will act accordingly. In a dialysis system, for example, where the ammonia level in the dialysate fluid is being monitored, a decrease of about 30% in the voltage output of the phototransistor might indicate that ammonia is building up in the dialysis system and that a dialysis treatment should be stopped. The controller 302 is also capable of operations such as recalibration of the photo detector 306, for example by periodically turning the photo detector 306 off to compensate for changes in ambient light.

This written description sets forth the best mode of the invention, and describes the invention so as to enable a person skilled in the art to make and use the invention, by presenting examples of the elements recited in the claims. The patentable scope of the invention is defined by the claims, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

The invention claimed is:

1. An ammonia gas detecting device comprising:
   a housing defining a fluid flow path including a fluid inlet, a fluid outlet, and an access port, the fluid flow path having first and second sections intersecting at a corner and the access port being located at the corner;
   a gas permeable/liquid impermeable membrane mounted on the housing at the access port such that the membrane is exposed to the fluid flow path;
   a seal installed between the membrane and the housing to block fluid from flowing outward of the access port around rather than through the membrane; and
   an ammonia sensor mounted on the housing at the access port in a position outward of the membrane.

2. An ammonia gas detecting device as defined in claim 1 wherein the housing is a unitary structure.

3. An ammonia gas detecting device as defined in claim 1 wherein the housing is made of plastic.

4. An ammonia gas detecting device as defined in claim 1 wherein the housing is configured to be connected to flexible tubing at the inlet and outlet ports.

5. An ammonia gas detecting device as defined in claim 1 wherein the seal is an O-ring.

6. An ammonia gas detecting device as defined in claim 1 wherein the access port comprises a cylindrical counterbore in which the seal, membrane, and ammonia sensor are installed.

7. An ammonia gas detecting device as defined in claim 1 wherein the ammonia sensor includes a mixture of bromocresol green and malonic acid.

8. An ammonia gas detecting device as defined in claim 1 further comprising a transparent adhesive securing the seal, membrane, and ammonia sensor to the housing.

9. An ammonia gas detecting device as defined in claim 1 further comprising a lens mounted on the housing at the access port in a position outward of the ammonia sensor.

10. An ammonia gas detecting device comprising:
    a housing defining a fluid flow path including a fluid inlet, a fluid outlet, and an access port, the fluid flow path having first and second sections intersecting at a corner and the access port being located at the corner and comprising a cylindrical counterbore with a shoulder surface extending radially inward;
    a gas permeable/liquid impermeable membrane installed in the counterbore such that the membrane is exposed to the fluid flow path and has an outer edge extending over the shoulder surface;
    an ammonia sensor installed in the counterbore in a position outward of the membrane; and
    a cylindrical lens installed in the counterbore in a position outward of the ammonia sensor such that a compressive force is exerted by and between an outer edge of the lens and the shoulder surface to seal the outer edge of the membrane against the shoulder surface and thereby to block fluid from flowing outward of the access port around rather than through the membrane.

11. An ammonia gas detecting device as defined in claim 10 wherein the lens has a cylindrical inner portion and a cylindrical outer rim portion, and the inner portion is thicker than the outer rim portion.

12. An ammonia gas detecting device as defined in claim 10 wherein the housing is a unitary structure.

13. An ammonia gas detecting device as defined in claim 10 wherein the housing is made of plastic.

14. An ammonia gas detecting device as defined in claim 10 wherein the housing is configured to be connected to flexible tubing at the inlet and the outlet ports.

15. An ammonia gas detecting device as defined in claim 10 wherein the ammonia sensor includes a mixture of bromocresol green and malonic acid.

16. An ammonia gas detecting device as defined in claim 10 further comprising a transparent adhesive securing the lens to the housing.

17. An ammonia gas detecting device as defined in claim 10 wherein the lens is secured to the housing by ultrasonic staking.

18. A system for monitoring the ammonia gas level in a fluid comprising:
   a) a housing including:
   i) a fluid flow path including a fluid inlet, a fluid outlet, and an access port,
   the fluid flow path having first and second sections intersecting at a corner and the access port being located at the corner;
   ii) a gas permeable/liquid impermeable membrane mounted on the housing at the access port such that the membrane is exposed to the fluid flow path;
   iii) a seal installed between the membrane and the housing to block fluid from flowing outward of the access port around rather than through the membrane; and
   iv) an ammonia sensor mounted on the housing at the access port in a position outward of the membrane;
   b) a light source directed at the ammonia sensor
   c) a photo detector operative to measure light reflected off the ammonia sensor from the light source; and
   d) a controller operative to cause the light source to emit light toward the ammonia sensor and to monitor an output from the photo detector.

19. A system as defined in claim 18 wherein the housing is a unitary structure.

20. A system as defined in claim 18 wherein the housing is made of plastic.

21. A system as defined in claim 18 wherein the housing is configured to be connected to flexible tubing at the inlet and outlet ports.

22. A system as defined in claim 18 wherein the seal is an O-ring.

23. A system as defined in claim 18 wherein the access port comprises a cylindrical counterbore into which the seal, membrane, and ammonia sensor are installed.

24. A system as defined in claim 18 wherein the ammonia sensor includes a mixture of bromocresol green and malonic acid.

25. A system as defined in claim 18 further comprising a transparent adhesive securing the seal, membrane, and ammonia sensor to the fluid flow path.

26. A system as defined in claim 18 further comprising a lens mounted on the housing at the access port in a position outward of the ammonia sensor.

27. A system as defined in claim 18 wherein the ammonia sensor is functional to change from yellow to blue as the ammonia sensor is exposed to ammonia gas.

28. A system as defined in claim 18 wherein the light source is a LED.

29. A system as defined in claim 18 wherein the light source is a yellow LED.

30. A system as defined in claim 18 wherein the photo detector is a phototransistor.

31. A system as defined in claim 18 wherein the photo detector is a light sensitive diode.

32. A system for monitoring the ammonia gas level in a fluid comprising:
   a) an ammonia gas detecting device comprising:
   i) a housing defining a fluid flow path including a fluid inlet, a fluid outlet,
   and an access port, the fluid flow path having first and second sections intersecting at a corner and the access port being located at the corner and comprising a cylindrical counterbore with a shoulder surface extending radially inward;
   ii) a gas permeable/liquid impermeable membrane installed in the
   counterbore such that the membrane is exposed to the fluid flow path and has an outer edge extending over the shoulder surface
   iii) an ammonia sensor installed in the counterbore in a position outward of the membrane; and
   iv) a cylindrical lens installed in the counterbore in a position outward of the ammonia sensor such that a compressive force is exerted by and between an outer edge of the lens and the shoulder surface to seal the outer edge of the membrane against the shoulder surface and thereby to block fluid from flowing outward of the access port around rather than through the membrane;
   b) a light source directed at the ammonia sensor;
   c) a photo detector operative to measure light reflected off the ammonia sensor from the light source; and
   d) a controller operative to cause the light source to emit light toward the ammonia sensor and to monitor an output from the photo detector.

33. A system as defined in claim 32 wherein the lens has a cylindrical inner portion and a cylindrical outer rim portion, and the inner portion is thicker than the outer rim portion.

34. A system as defined in claim 32 wherein the housing is a unitary structure.

35. A system as defined in claim 32 wherein the housing is made of plastic.

36. A system as defined in claim 32 wherein the housing is configured to be connected to flexible tubing at the inlet and outlet ports.

37. A system as defined in claim 32 wherein the ammonia sensor includes a mixture of bromocresol green and malonic acid.

38. A system as defined in claim 32 further comprising a transparent adhesive securing the lens to the housing.

39. A system as defined in claim 32 wherein the lens is secured to the housing by ultrasonic staking.

40. A system as defined in claim 32 wherein the ammonia sensor is functional to change from yellow to blue as the ammonia sensor is exposed to ammonia gas.

41. A system as defined in claim 32 wherein the light source is a LED.

42. A system as defined in claim 32 wherein the light source is a yellow LED.

43. A system as defined in claim 32 wherein the photo detector is a phototransistor.

44. A system as defined in claim 32 wherein the photo detector is a light sensitive diode.

45. An ammonia gas detecting device as defined in claim 1 wherein the access port defines a plane and the angles of the flow paths defined by the first and second sections are each about 30 degrees relative to the plane defined by the access port.

46. An ammonia gas detecting device as defined in claim 10 wherein the access port defines a plane and the angles of the flow paths defined by the first and second sections are each about 30 degrees relative to the plane defined by the access port.

47. A system as defined in claim 18 wherein the access port defines a plane and the angles of the flow paths defined by the first and second sections are each about 30 degrees relative to the plane defined by the access port.

48. A system as defined in claim 32 wherein the access port defines a plane and the angles of the flow paths defined by the first and second sections are each about 30 degrees relative to the plane defined by the access port.

49. A system as defined in claim 18, wherein the controller is further operative to control the light source and photo detector to calibrate the photo detector by periodically turning the photo detector off to compensate for changes in ambient light.

50. A system as defined in claim 32, wherein the controller is further operative to control the light source and photo detector to calibrate the photo detector by periodically turning the photo detector off to compensate for changes in ambient light.

* * * * *

UNITED STATES PATENT AND TRADEMARK OFFICE
CERTIFICATE OF CORRECTION

| | | |
|---|---|---|
| PATENT NO. | : 8,409,864 B2 | Page 1 of 1 |
| APPLICATION NO. | : 11/443709 | |
| DATED | : April 2, 2013 | |
| INVENTOR(S) | : Stephen R. Ash | |

It is certified that error appears in the above-identified patent and that said Letters Patent is hereby corrected as shown below:

In the Claims:

Column 7, line 30 (Claim 18, line 30), delete "sensor" and insert --sensor;--.

Column 8, line 16 (Claim 32, line 16), delete "surface" and insert --surface;--.

Signed and Sealed this
Fourth Day of June, 2013

Teresa Stanek Rea
*Acting Director of the United States Patent and Trademark Office*